United States Patent
Picard et al.

(10) Patent No.: US 11,613,520 B2
(45) Date of Patent: Mar. 28, 2023

(54) ELECTROLYTES FOR ELECTROCHEMICAL GENERATOR

(71) Applicant: COMMISSARIAT A L'ENERGIE ATOMIQUE ET AUX ENERGIES ALTERNATIVES, Paris (FR)

(72) Inventors: Lionel Picard, Grenoble (FR); Laurent Bernard, Grenoble (FR); Sandrine Lyonnard, Grenoble (FR); Hakima Mendil, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 292 days.

(21) Appl. No.: 16/751,856

(22) Filed: Jan. 24, 2020

(65) Prior Publication Data
US 2020/0239413 A1    Jul. 30, 2020

(30) Foreign Application Priority Data

Jan. 29, 2019 (FR) ..................... 1900799

(51) Int. Cl.
| | |
|---|---|
| *C07C 309/47* | (2006.01) |
| *C07C 307/02* | (2006.01) |
| *H01M 10/052* | (2010.01) |
| *H01M 10/0566* | (2010.01) |
| *H01M 10/056* | (2010.01) |
| *C07C 311/48* | (2006.01) |
| *C09K 19/32* | (2006.01) |
| *C09K 19/40* | (2006.01) |
| *H01M 10/054* | (2010.01) |

(52) U.S. Cl.
CPC .......... *C07C 309/47* (2013.01); *C07C 307/02* (2013.01); *C07C 311/48* (2013.01); *C09K 19/322* (2013.01); *C09K 19/40* (2013.01); *H01M 10/052* (2013.01); *H01M 10/056* (2013.01); *H01M 10/0566* (2013.01); *H01M 10/054* (2013.01); *H01M 2300/0025* (2013.01); *H01M 2300/0045* (2013.01)

(58) Field of Classification Search
None
See application file for complete search history.

(56) References Cited

U.S. PATENT DOCUMENTS

2018/0261886 A1* 9/2018 Picard ............... H01M 10/0525

FOREIGN PATENT DOCUMENTS

| EP | 3 353 262 A1 | 8/2018 | |
|---|---|---|---|
| WO | WO-2017050769 A1 * | 3/2017 | ........... C07C 309/76 |

OTHER PUBLICATIONS

Bouchet, R. et al., "Single-ion BAB Triblock Copolymers as Highly Efficient Electrolytes for Lithium-Metal Batteries", Nature Materials,XP055316945, vol. 12, No. 5, pp. 452-457, (Mar. 31, 2013).
Cohen, M., et al. "Molecular Transport in Liquids and Glasses", The Journal of Chemical Physics, vol. 31, pp. 1164, (1959).
French Search Report issued by the French Patent Office in corresponding French Application No. 1900799, dated Oct. 8, 2019.
Jo, G., et al. "Simple Route for Tuning the Morphology and Conductivity of Polymer Electrolytes: One End Functional Group is Enough", ACS Macro Letters, vol. 2, pp. 990-995, (2013).
Jung, H, et al., "Modulating Ion Transport and Self-Assembly of Polymer Electrolytes via End-Group Chemistry", Macromolecules, vol. 50, pp. 3224-3233, (2017).
Meziane, R. et al., "Single-ion Electrolytes Based on a Delocalized Polyahion for Lithium Batteries", Electrochimica Acta, vol. 57, pp. 14-19 (2011).
Tominaga, Y. et al., "High Ionic Conductivity of PEO/ Sulfonamide Salt Hybrids", Solid State Ionics, vol. 124, pp. 323-329 (1999).

* cited by examiner

*Primary Examiner* — Robert S Carrico
(74) *Attorney, Agent, or Firm* — ArentFox Schiff LLP

(57) ABSTRACT

The present invention relates to thermotropic ionic liquid crystal molecules of general formula (I)

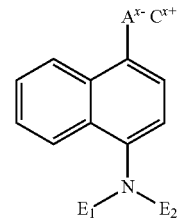

With $E_1$ and $E_2$, which may be identical or different, representing, independently of one another, a linear, saturated and unsubstituted $C_{10}$ to $C_{14}$ hydrocarbon-based radical, $A^{x-}$ representing a sulfonate anion or a sulfonylimide anion of formula $-SO_2-N^- -SO_2C_yF_{2y+1}$ with y being an integer ranging from 0 to 2 and $C^{x+}$ a sodium, lithium or potassium ion, most particularly advantageous for their conductivity performance qualities as an electrolyte in particular for lithium batteries.

14 Claims, 3 Drawing Sheets

[Fig.1]
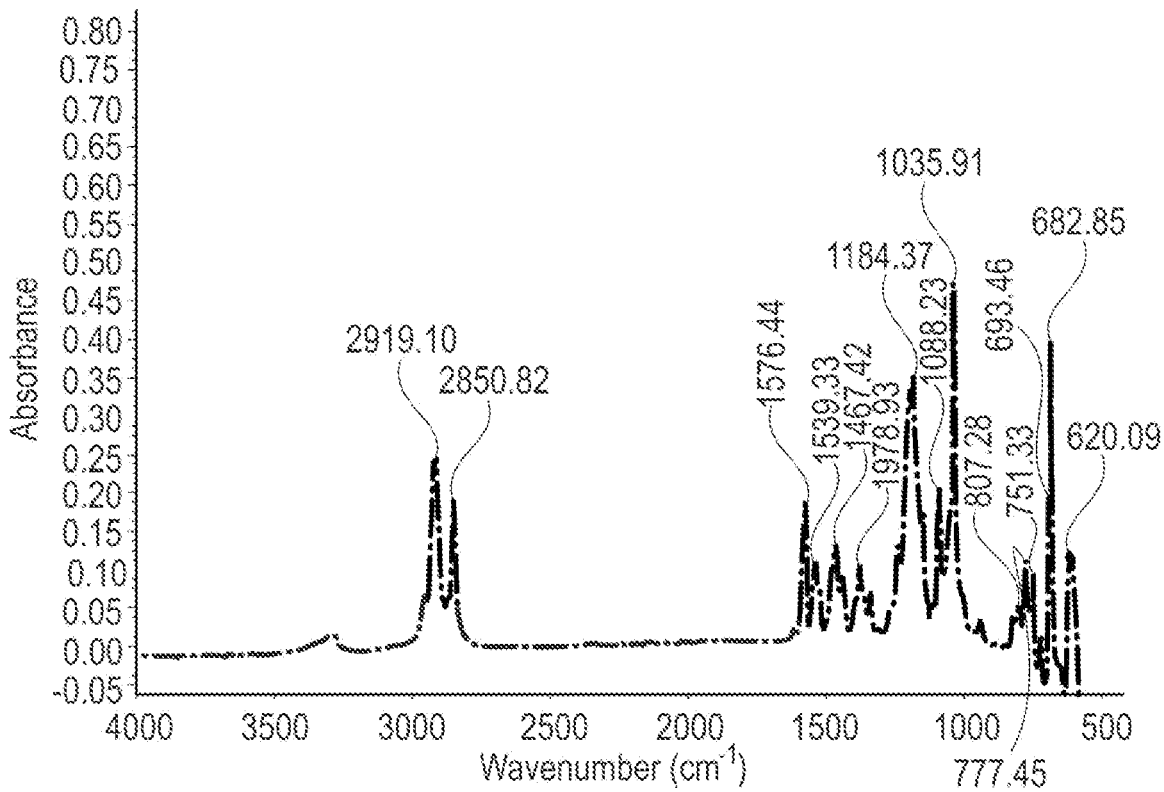
[Fig 2]
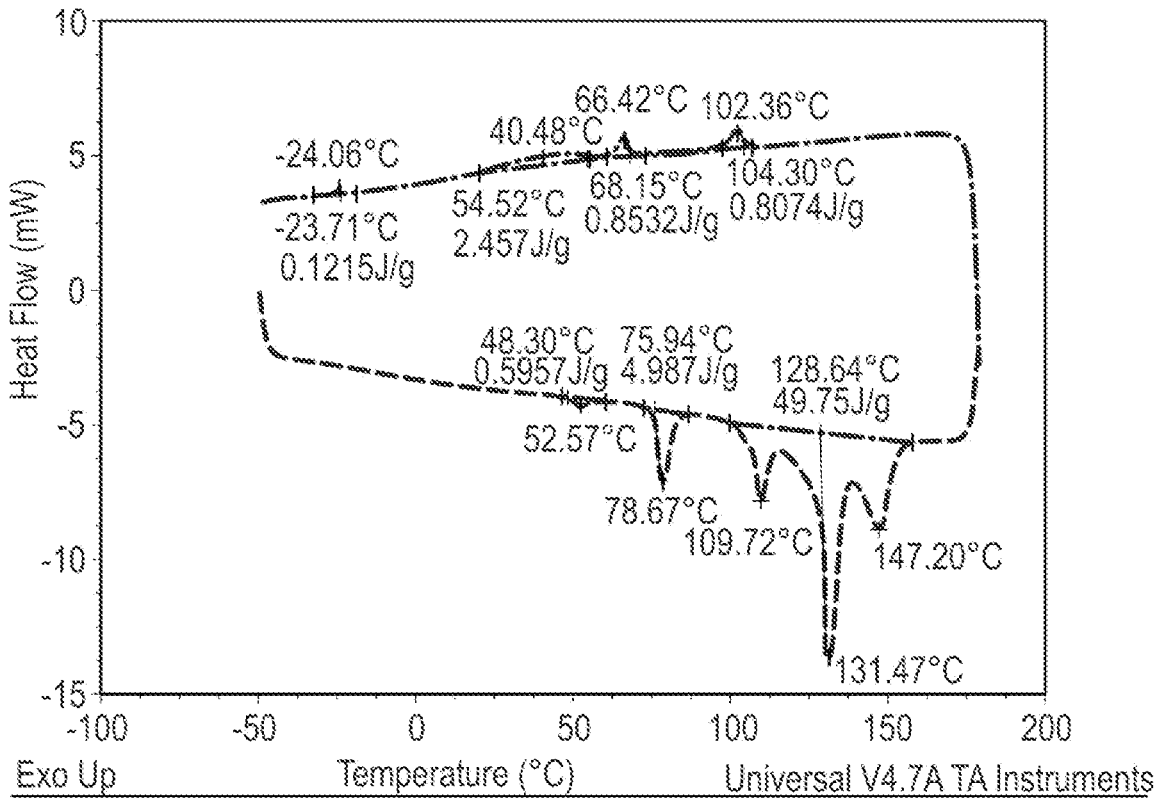

[Fig 3]
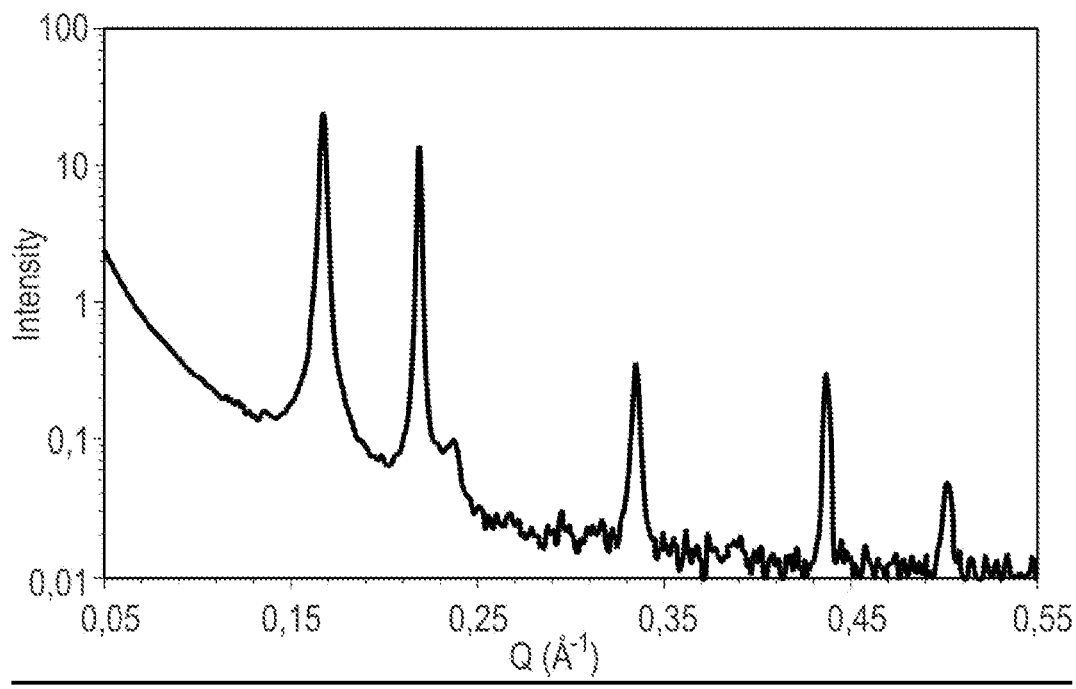
[Fig 4]
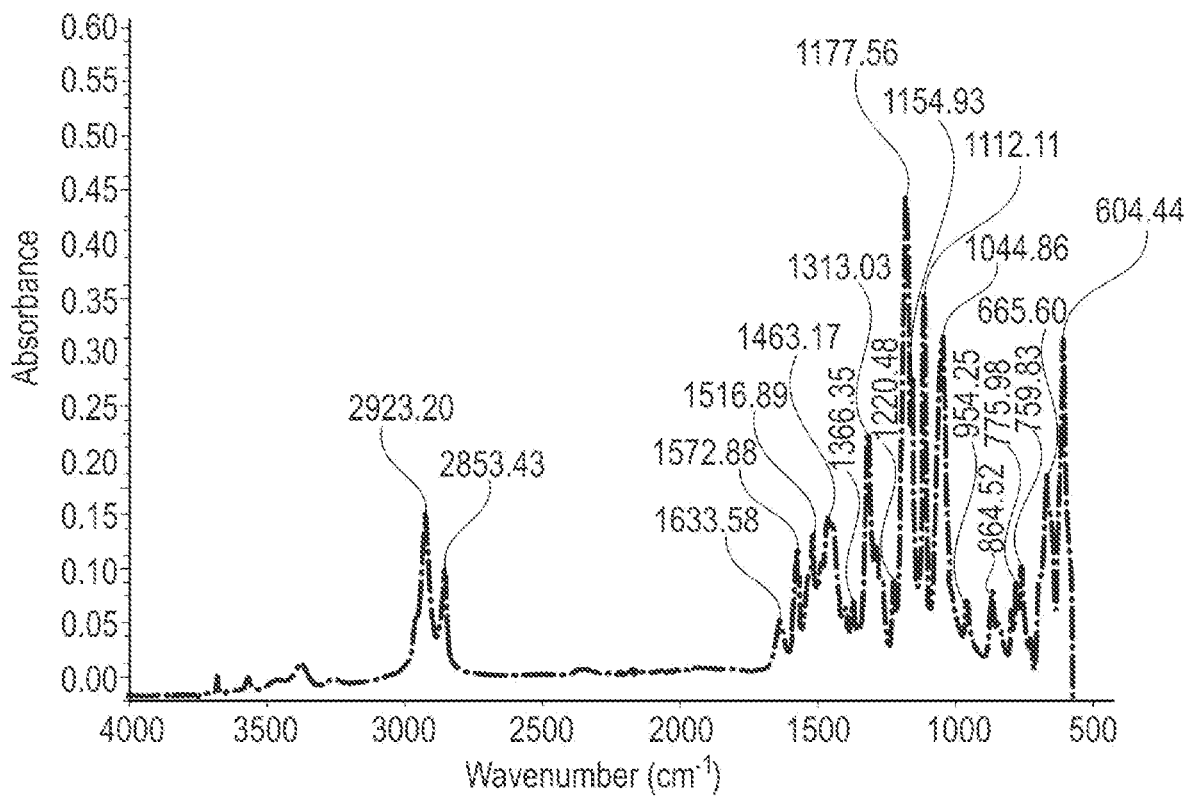

[Fig 5]
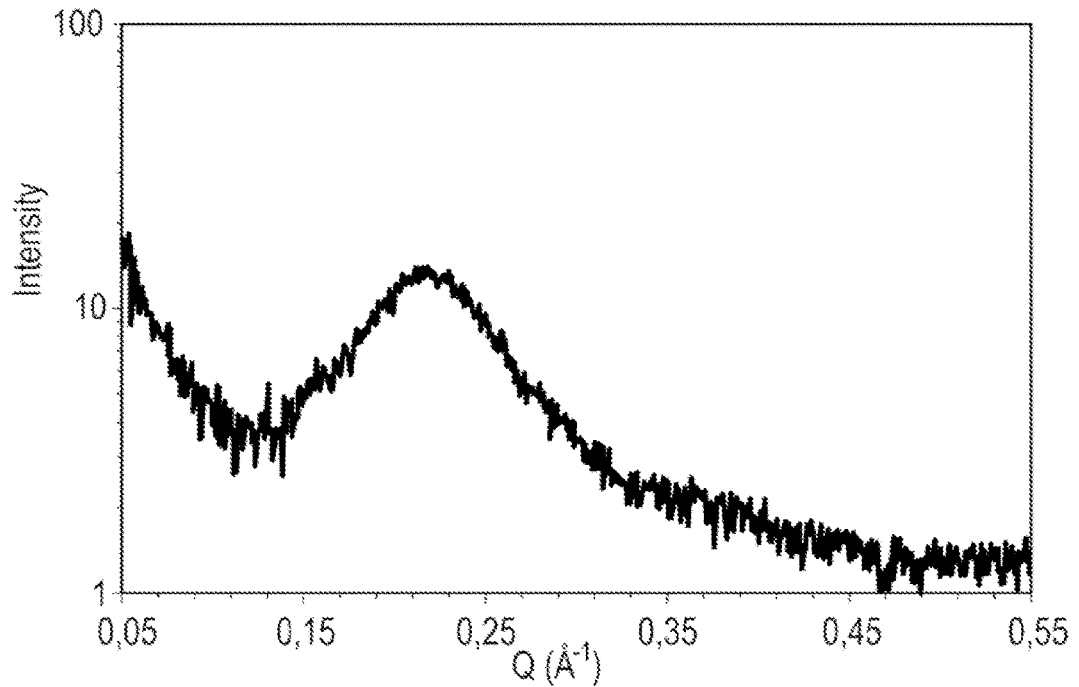
[Fig 6]
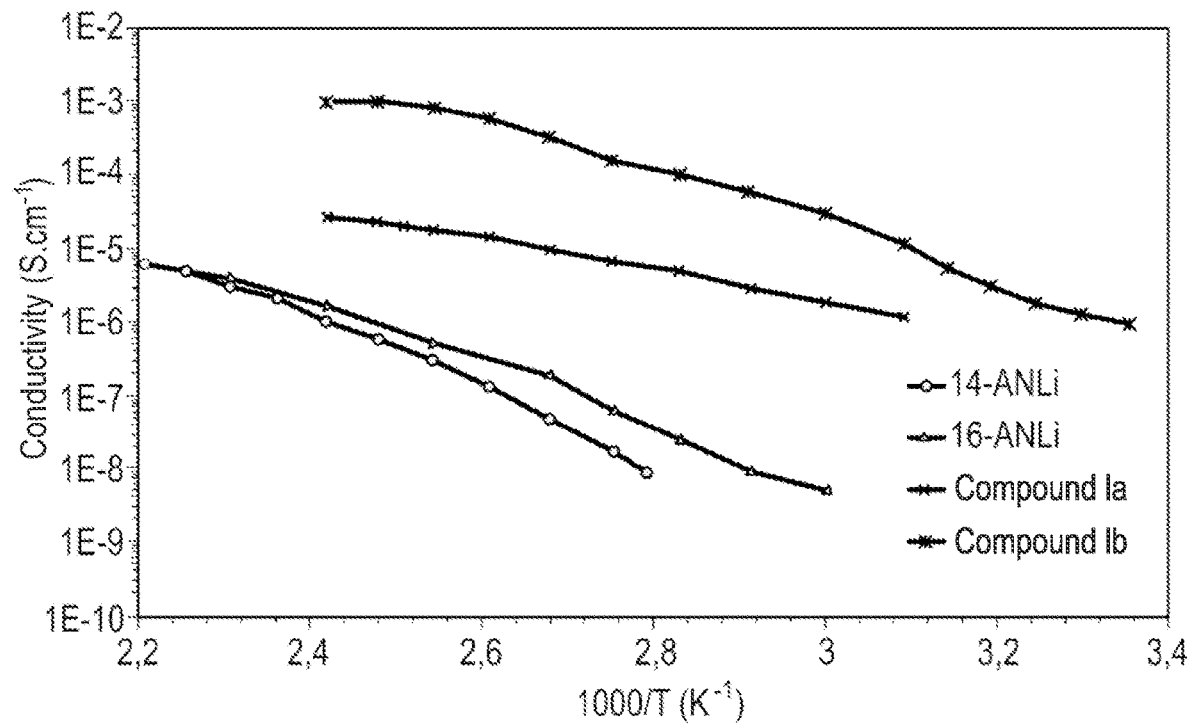

ELECTROLYTES FOR ELECTROCHEMICAL GENERATOR

CROSS-REFERENCE TO RELATED APPLICATION

This application claims priority to French Patent Application No. 19 00799, filed on Jan. 29, 2019. The disclosure of the priority application is incorporated in its entirety herein by reference.

TECHNICAL FIELD

The present invention relates to novel compounds which can be used as electrolytes, in particular in electrochemical storage or generation systems.

Such electrolytes may be used in various electrochemical systems or devices, in particular in lithium batteries.

PRIOR ART

Conventionally, the operating principle of an electrochemical generator is based on the insertion and removal, also called "deinsertion", of an alkali metal ion or of a proton, into and from the positive electrode, and the deposition or extraction of this ion, onto and from the negative electrode.

The main systems use the lithium cation as the ionic transport species. In the case of a lithium accumulator for example, the lithium cation extracted from the cathode, during charging of the battery, is deposited on the anode and conversely, it is extracted from the anode so as to be intercalated in the cathode during discharging. The transport of the proton or of the alkali or alkaline-earth cation, in particular the lithium cation, between the cathode and the anode is ensured by an ion-conducting electrolyte.

The formulation of the electrolyte used is a factor that is essential to the performance qualities of the electrochemical system, in particular when said system is used at very low or very high temperatures. The ion conductivity of the electrolyte conditions in particular the efficiency of the electrochemical system given that it is involved in the mobility of the ions between the positive and negative electrodes.

Other parameters are also involved in the choice of the electrolyte used. These factors are in particular its thermal, chemical or electrochemical stability in the electrochemical system, and also economic, safety and environmental protection criteria, including in particular the toxicity of the electrolyte.

In general, the electrolytes of electrochemical systems are in liquid, gelled or solid form.

With regard to the electrolytes in liquid form, the conventional electrolytes of electrochemical generators with a metal cation from one of the first two columns of the periodic table of elements, for example a lithium cation, are compounds of a salt of this cation dissolved in an organic or aqueous medium (conventionally in carbonate solvents or acetonitrile for lithium batteries), in the presence or absence of additives.

In particular, conventional supercapacitor electrolytes are compounds of an organic salt (conventionally a tetraethylammonium tetrafluoroborate salt $Et_4N-BF_4$) dissolved in acetonitrile. Their use as a complete electrochemical storage system, for example in an Li-ion battery, requires, however, the addition of a separator in order to ensure electrical insulation between the positive and negative electrodes. Nevertheless, even though these electrolytes have good ion conductivities, there are still safety and cost problems in the context of the use of organic solvents (low thermal stability), and of electrochemical stability in the context of the use of an aqueous medium.

As electrolyte, mention may also be made of the electrolytic membrane of electrochemical generator systems of proton-exchange-membrane fuel cell type, conventionally consisting of a polymer with a fluorocarbon main chain bearing pendent groups comprising sulfonic acid functions, such as Nafion®. However, at the current time, the use of polymers of this type for proton conduction requires control of the degree of hydration of the membrane in order to obtain the desired performance qualities. This type of polymer is a semicrystalline polymer, the only amorphous part of which has conduction properties, the crystalline part conferring the mechanical properties required for it to operate in a complete system.

A mixture of a polystyrene bearing sulfonyl(trifluoromethylsulfonyl)imide and POE groups for producing an electrolyte membrane has also been proposed (Meziane et al. Electrochimica Acta, 2011, 57, 14-19). However, these polymer electrolytes have insufficient ion conductivities, of about $9.5 \times 10^{-6}$ S·cm$^{-1}$ at 70° C. Furthermore, for most of the current fields of application, it is not possible to use working temperatures above 70° C.

For lithium electrolyte systems, the incorporation of a lithium bis(trifluoromethane)sulfonimide salt (LiTFSI) into the repeating unit, together with styrene, so as to form poly(styrene trifluoromethanesulfonylimide lithium) P(STFSILi), has also been considered. At the end of the polymerization, the poly(electrolyte) has a BAB block copolymer architecture comprising a central block "A" of PEO. The maximum conductivity, of about $10^{-5}$ S·cm$^{-1}$, is obtained at 60° C. with a polymer comprising 78% by weight of POE (R Bouchet et al., Nature Materials (2013), 12, 452). The incorporation of a functional group at the end of a block copolymer of this type has proven to be beneficial for its conductivity (G. Lo et al., ACS Macro Lett. (2013), 2, 990 and H. Jung et al., Macromolecules (2017), 50, 3224).

In another electrolyte variant, sulfonamides have also been considered for the development of (co)-solvents for lithium-ion batteries. These compounds essentially have a bond between the sulfur atom of the sulfonamide comprising short fluorinated alkyl chains and the nitrogen atom of this sulfonamide comprising simple hydrocarbon-based functions (D Bresser et al. EP 3 050 872). For its part, the publication H. Ohno et al. (Solid State Ionics (1999), 124, 323) describes compounds in which the sulfonamide unit is bonded, by its nitrogen atom, to a phenyl. This asymmetrical salt can also be connected, via the sulfur atom of the sulfonamide anion, to a polymer of PEO type (550 g/mol).

More recently, the inventors have characterized the improved conductivity performance qualities of sulfonamide derivatives consisting of aromatic functions, functionalized, on the one hand, with a sulfonamide unit and, on the other hand, with an amine function (EP 3 353 262). The chemical structures explicitly described have an amine function bearing two dihydroxylated $C_4$ to $C_{18}$ alkyl chains and reveal a conductivity that can reach up to $2 \times 10^{-7}$ S·cm$^{-1}$ at 100° C.

SUMMARY OF THE INVENTION

Against all expectations, the inventors have at the current time discovered that sulfonamide derivates related to those described in said patent EP 3 353 262 prove to be even more advantageous in terms of performance qualities. They have a high ion conductivity and preferably a transport number that is even closer to unity.

Thus, the first subject of the present invention is ionic liquid crystal molecules corresponding to general formula (I)

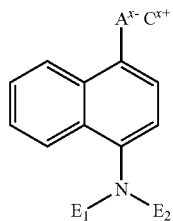

[Chem 1]

wherein $E_1$ and $E_2$, which may be identical or different, represent, independently of one another, a linear, saturated and unsubstituted $C_{10}$ to $C_{14}$ hydrocarbon-based radical, $A^{x-}$ represents a sulfonate anion or sulfonylimide anion of —$SO_2$—$N^-$—$SO_2C_yF_{2y+1}$ with y being an integer ranging from 0 to 2 and $C^{x+}$ represents a countercation of the anionic group -$A^{x-}$, chosen from sodium, lithium and potassium ions, and is preferably a lithium ion.

The term "ionic liquid crystal" is intended to mean a liquid crystal bearing at least one ionic group, like the $A^{x-}C^{x+}$ unit required according to the invention.

The ionic liquid crystal in accordance with the invention is thermotropic.

It is recalled that a thermotropic liquid crystal is defined by three types of successive states, in which it exists as a function of the temperature. Below its melting point, it is in a crystalline state (or crystalline phase). Then, above its melting point, it passes into a mesomorphic state consisting of a mesophase or of a succession of mesophases. Finally, above its clarification temperature, it passes into an isotropic state (or amorphous phase).

The term "melting point" is intended to mean the temperature at which a thermotropic liquid crystal passes from a crystalline state to a mesomorphic state.

The term "clarification temperature" is intended to mean the temperature at which a thermotropic liquid crystal leaves its mesophase or its last mesophase of a succession of mesophases to enter an isotropic (or liquid) state.

The term "mesomorphic state" is intended to mean the state in which a thermotropic liquid crystal is found when it is brought to a temperature above its melting point and below its clarification temperature.

As illustrated in the examples that follow, the inventors have shown that, when the ionic liquid crystal molecules of the invention are in a mesomorphic state, they have an ion conductivity that can reach up to $3.2 \times 10^{\prime}$S·cm$^{-1}$ at 100° C., i.e. a value greater by at least a factor of 1000 compared with those observed for the compounds described in document EP 3 353 262.

The temperature range in which a thermotropic liquid crystal molecule is in a mesomorphic state can be determined by means of a method known to those skilled in the art, such as for example DSC ("Differential Scanning calorimetry").

The nature of the mesophases of a mesomorphic state can be determined by a combination of other characterizations, such as POM (Polarized light Optical Microscopy), by XRD (X-Ray Diffraction) and/or by SAXS ("Small Angle X-ray Scattering"), the latter generally being used in addition to XRD.

According to another of its aspects, the invention also relates to the use of a thermotropic ionic liquid crystal molecule as defined above, in a mesomorphic state, as an electrolyte in an electrochemical system.

The invention also relates to an electrolyte comprising, or even being formed of, thermotropic ionic liquid crystal molecules as defined above, in a mesomorphic state.

The molecules according to the invention can be used as electrolytes in numerous electrochemical systems, such as generators, for example lithium batteries.

The use of the molecules according to the invention as electrolytes proves to be advantageous in several respects.

First of all, since these molecules are ion-conducting in a mesomorphic state, they have a greatly broadened working temperature as an electrolyte, which can be within the entire temperature range in which the molecules are in a mesomorphic state, which generally corresponds to the temperature range between the melting point and the clarification point. The molecules of the invention can also be ion-conducting at a temperature above their clarification temperature.

An electrochemical system, for example a lithium battery, produced from an electrolyte according to the invention, can thus operate over a wide temperature range, preferably between −60° C. and +300° C., and more preferentially between −20° C. and +200° C.

Moreover, the ion conductivity of an electrolyte according to the invention is based on a "direct" conduction mechanism, by "hopping" of the $C^{x+}$ cations from one anionic group $A^{x-}$ to the other, and not based on an assisted mechanism as is the case, for example, with the polymer electrolytes proposed by Cohen et al. Molecular Transport in Liquids and Glasses, J. Chem. Phys. 31, 1164 (1959).

As emerges from the examples below, an electrolyte according to the invention thus results in significantly improved performance qualities in terms of ion conductivity.

Other characteristics, variants and advantages of the molecules and electrolytes according to the invention, of the preparation thereof and of the use thereof will emerge more clearly on reading the description, the examples and the figures that will follow, given by way of nonlimiting illustration of the invention.

In the remainder of the text, the expressions "between . . . and . . . ", "extending from . . . to . . . " and "ranging from . . . to . . . " are equivalent and are intended to mean that the limits are included, unless otherwise mentioned.

Unless otherwise indicated, the expression "comprising a" should be understood to mean "comprising at least one".

Molecules of the Invention

As mentioned above, the thermotropic ionic liquid crystal molecules according to the invention correspond to general formula (I)

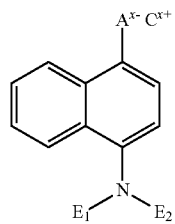

[Chem 2]

wherein $E_1$ and $E_2$, which may be identical or different, represent, independently of one another, a linear, saturated and unsubstituted $C_{10}$ to $C_{14}$ hydrocarbon-based radical, $A^{x-}$ represents the sulfonate anion, or a sulfonylimide anion of $-SO_2-N^--SO_2C_yF_{2y+1}$ with y being an integer ranging from 0 to 2 and $C^{x+}$ represents a countercation of the anionic group $-A^{x-}$, chosen from sodium, lithium and potassium cations, and preferably lithium cations.

In the context of the invention, the hydrocarbon-based radicals represented by $E_1$ and $E_2$ are generally identical and preferably chosen from unsubstituted linear alkyl radicals such as decyl, undecyl, dodecyl, tridecyl and tetradecyl.

In particular, the hydrocarbon-based radical represented by $E_1$ or $E_2$ is a $C_{11}$ to $C_{13}$ radical and more preferentially is dodecyl.

According to one embodiment, $A^{x-}$ is the sulfonate anion.

According to another embodiment, $-A^{x-}$ is the anion of formula $-SO_2-N^--SO_2-CF_3$.

According to another implementation variant of the invention, $C^{x+}$ represents the $Li^+$ cation.

According to this variant, the group $-A^{x-}C^{x+}$ preferably represents an $-SO_3^-Li^+$ group.

As detailed in the remainder of the text, such molecules can advantageously be used as electrolyte in a lithium battery.

Preferably, the thermotropic ionic liquid crystal molecules in accordance with the invention are not used in the form of polymers.

Thus, the thermotropic ionic liquid crystal molecules in accordance with the invention have a molecular weight of less than or equal to 1 500 g/mol, preferentially less than 1 000 g/mol.

A subject of the present invention is in particular the following thermotropic ionic liquid crystal molecules, which are particularly suitable for use as an electrolyte:

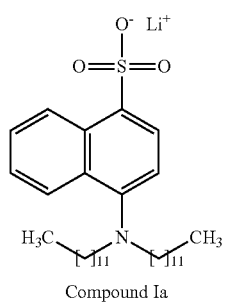

Compound Ia

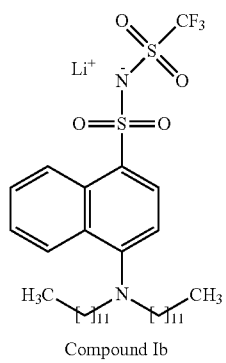

Compound Ib

Preparation of the Compounds of the Invention

The molecules according to the invention can be prepared by carrying out nucleophile substitution or additional methods known to those skilled in the art, as detailed below.

The molecules of the invention can be prepared by bringing together a precursor of the naphthalene unit and a precursor of the dialkylamine function, under conditions conducive to their interaction according to a nucleophilic substitution or addition reaction known to those skilled in the art. This synthesis can in particular be carried out by taking into consideration the protocols described in document EP 3 353 262 and the preparation processes detailed below for compounds Ia and Ib.

Use as Electrolyte

The thermotropic ionic liquid crystal molecules according to the invention can advantageously be used, in a mesomorphic state, as an electrolyte in an electrochemical system.

As mentioned above, a mesomorphic state denotes the mesophase or the succession of mesophases in which the thermotropic ionic liquid crystal molecules according to the invention exist as a function of their temperature, lying between the melting point and the clarification temperature.

The electrolyte formed of such molecules is advantageously used in combination with a porous separator onto which said electrolyte is impregnated, said separator providing physical separation between the two electrodes of the electrochemical system.

As a separator, use may be made of any porous separator conventionally used in an electrochemical system, such as for example a porous separator of a lithium battery or an ion-exchange membrane of a fuel cell. Those skilled in the art are able to select a separator suitable for the use of the electrolyte.

The thermotropic ionic liquid crystal molecules according to the invention wherein $C^{x+}$ represents an $Li^+$ cation can advantageously be used, in a mesomorphic state, as an electrolyte in a lithium battery.

Electrolyte

Thus, according to another of its aspects, the present invention relates to an electrolyte comprising, or even being formed of, thermotropic ionic liquid crystal molecules as defined below, in a mesomorphic state.

In the electrolyte of the invention, the thermotropic ionic liquid crystal molecules are preferably used at a temperature of from 80° C. to 220° C., generally of from 100° C. to 200° C., preferentially of from 130° C. to 170° C., for example of about 150° C.

Preferably, the liquid electrolyte of the invention has a viscosity of greater than or equal to 10 mPa·s, preferably of from 100 mPa·s to 100 Pa·s, at a temperature of between −60° C. and 300° C.

The expression "at a temperature of between −60° C. and 300° C." is intended to mean that the liquid electrolyte of the invention has a viscosity as defined above at at least one temperature lying in this range. This does not necessarily mean that the liquid electrolyte of the invention has a viscosity as defined above at any temperature lying in this range.

The viscosity can be measured by extrapolation to zero shear from the curve of viscosity as a function of the shear gradient at a given temperature, measured on a cone/plate or plate/plate viscosimeter/rheometer.

This condition with regard to the viscosity of the liquid electrolyte ensures good impregnation thereof into the separator of the electrochemical system.

The electrolyte according to the invention has good ionic conductivity properties.

In particular, the electrolyte of the invention advantageously has an ionic conductivity at 20° C. of greater than or equal to $10'S \cdot cm^{-1}$. In particular, an electrolyte according to the invention can advantageously have an ionic conductivity of greater than $10'S \cdot cm^{-1}$ at 100° C. and an ionic conductivity at 150° C. of greater than or equal to $10^{-3}$ $S \cdot cm^{-1}$.

The ionic conductivity can be measured by voltage-dependent or current-dependent electrochemical impedance spectroscopy, according to a method known to those skilled in the art.

Electrochemical System

The electrolyte according to the invention can be used in an electrochemical system, for example for a lithium battery.

According to yet another of its aspects, the present invention thus relates to an electrochemical system comprising an electrolyte according to the invention.

In the electrochemical system of the invention, the electrolyte is preferably impregnated onto a porous separator as described above.

The electrochemical system may be an electrochemical storage, converter or generator system.

It may more particularly be a primary or secondary battery, for example a lithium, sodium or potassium battery; a lithium-air or lithium-sulfur accumulator.

According to one particular embodiment, the electrolyte is used in a battery, in particular a lithium battery.

According to yet another of its aspects, the present invention also relates to a porous separator impregnated with an electrolyte according to the invention.

Such a porous separator is particularly suitable for use in an electrochemical system as described above.

The invention will now be described by means of the following examples and figures, given of course in a manner that illustrates and does not limit the invention.

BRIEF DESCRIPTION OF THE DRAWINGS

FIG. 1: FTIR analysis of compound Ia.
FIG. 2: calorimetric analysis of compound Ia by DSC under argon and with a heating rate of 10° K/min
FIG. 3: Analysis of compound Ia by SAXS.
FIG. 4: FTIR analysis of compound Ib.
FIG. 5: Analysis of compound Ib by SAXS.
FIG. 6: Ion conductivity analysis, in temperature increase and temperature decrease, of compounds Ia and Ib versus products not in accordance with the invention.

EXAMPLE 1

Preparation of Compound Ia in Accordance with the Invention

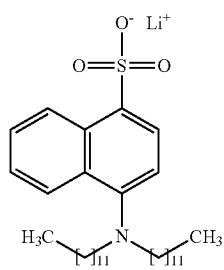

[Chem 5]

1.25 g of 4-aminonaphthalenesulfonic acid, 3.50 g of 1-bromododecane and 2.3 ml of triethylamine are dissolved in 50 ml of DMF. The solution is stirred at 70° C. for 48 h. 40 ml of deionized water and 2 ml of 2 M HCl aqueous solution are added thereto and the aqueous phase is extracted three times with 30 ml of dichloromethane. The product is purified on a silica column (MeOH/DCM) and the fractions containing the desired product are combined and evaporated. 1.74 g of disubstituted product is obtained in the form of a yellowish powder. Following neutralization with a dilute solution of LiOH, the product A is obtained.

Characterization of the Liquid Crystal

$^1$HNMR (400 MHz; MeOD; 300 K): δ ppm 8.7 (d, 1H); 8.0 (d, 1H); 7.9 (d, 1H); 7.5 (dd, 1H); 7.4 (dd, 1H); 6.5 (d, 1H); 3.2 (d, 2H); 3.0 (d, 2H); 1.4 (m, 40H); 0.88 (t, 6H)

$^{13}$C NMR (400 MHz; MeOD; 300 K): δ ppm 131.6; 129.0; 128.1; 127.3; 125.4; 124.9; 122.0; 101.6; 53.8; 44.8; 33.1; 30.8; 30. 7; 30.5; 29.9; 28.5; 23.8; 22.6; 14.4; 7.6

Its ATR 2-FTIR spectrum recorded on a Thermo Scientific Nicolet 6700 apparatus is represented in FIG. 1.

The product Ia was characterized by DSC under argon and with a heating rate of 10° K/min. The results of the calorimetric analysis are represented in FIG. 2. The analysis is carried out with a temperature gradient of 10° C./min under an inert atmosphere. The sample is heated from ambient temperature to 180° C. during a first heating not represented in FIG. 2, then a cooling cycle down to −50° C., followed by a second heating up to 180° C. is applied and the points measured are represented below.

The product shows five transitions in heating at 52° C., 78° C., 109° C., 131.5° C. and 147.2° C., and four in cooling at 102° C., 66.4° C., 40.5° C. and −24° C.

For the SAXS analysis, a sample of powder of compound Ia is placed between two kapton films under an inert atmosphere and measured on a SAXS line. A rotating copper anode and a Vantec 2000 detector are used. The signal obtained is a ring of equivalent density (therefore the material is isotropic); after radial integration, the 2D spectrum represented in FIG. 3 is obtained. The organized state of this material is characterized by the presence of thin and intense Bragg peaks. The SAXS image of the product Ia corresponds to a columnar rectangular structure at ambient temperature.

EXAMPLE 2

Synthesis of Compound Ib

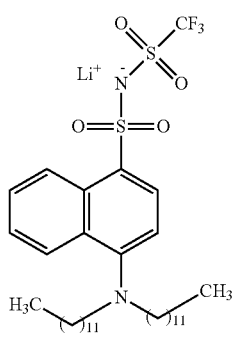

[Chem 6]

Synthesis of the ANTFSI Synthon:

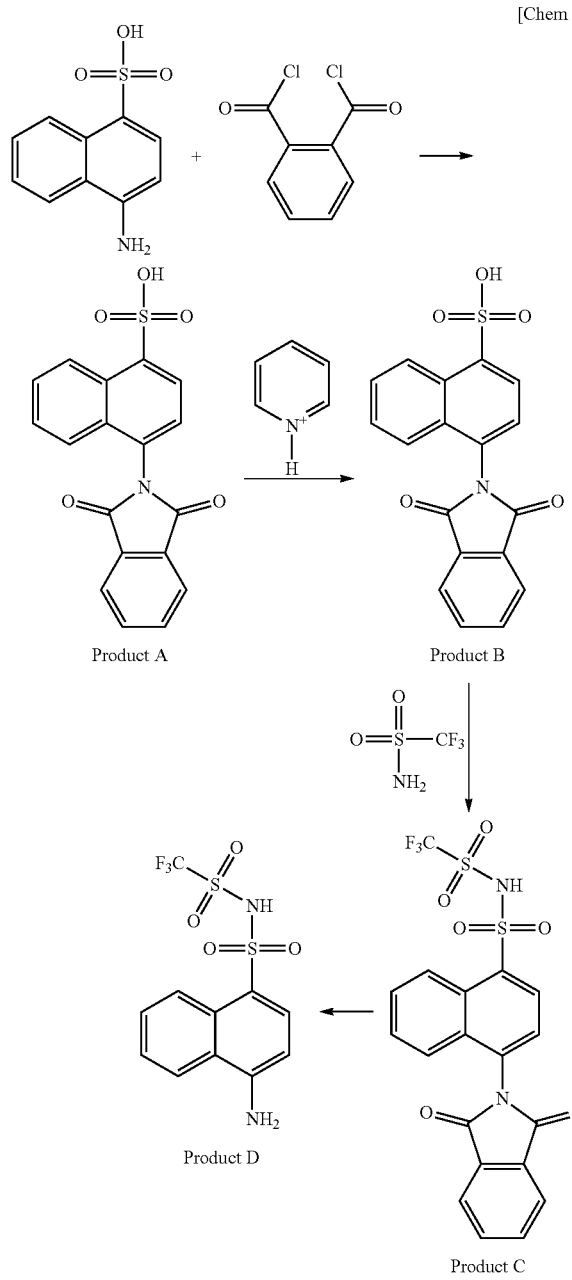

Step n°1:

Amino-4-naphthalenesulfonic acid—ANH (14.97 g, 67.13 mmol) is weighed into a 500 ml single-necked round-bottomed flask under an inert atmosphere. 100 ml of pyridine are added dropwise to the ANH still under an inert atmosphere, then 13 ml (1.3 eq) of phthaloyl chloride are added with stirring. As soon as the first drop of phthaloyl chloride is added, fumes are given off and the solution begins to turn amber in color. The reaction medium is stirred at reflux for 24 h. The pyridine is evaporated off and the residue is recrystallized three times from methanol until the product A is obtained (21.698 g, 75% yield after purification).

Step n°2:

The product A (21.698 g, 50.290 mmol) is added to 100 ml of anhydrous DMF in a three-necked 500 ml round-bottomed flask inserted under argon. Once the product has dissolved, the reaction medium is placed in an ice bath at 3-5° C. and thionyl chloride (7.5 ml, 2 eq) is added dropwise via a dropping funnel. At the end of the addition, the reaction medium is reheated to ambient temperature with stirring. After reaction for 1 h, the reaction medium is poured dropwise into cold water. The product 2 is filtered through a Buchner funnel and dried under vacuum at 80° C. for 12 h. The product B obtained is a white powder (22.7 g, 98% yield).

Step n°3:

The product B (22.7 g, 61.0 mmol) is added to 200 ml of anhydrous acetone contained in a single-necked 500 ml round-bottomed flask. Trifluoromethanesulfonamide (34.4 g, 2 eq) and, finally, triethylamine (20 ml, 2.5 eq) are then added. The reaction medium is stirred at ambient temperature for 24 h; according to the thin layer chromatography (TLC) carried out with the 1:1 mixture of DCM/MeOH solvent as eluent, the conversion of the product 2 is total. The solvent and the excess triethylamine are evaporated off under reduced pressure and the dry residue is purified on a silica column. The product C is obtained (35.97 g, 95% yield).

Step n°4:

The product C (1 g, 2.1 mmol) is placed in a 500 ml single-necked round-bottomed flask. 300 ml of anhydrous acetone are added in order to totally dissolve the product 3. Hydrazine (2 eq) is then added to the reaction medium which is subsequently stirred for 24 h at ambient temperature. The formation of a white precipitate during the reaction is noted. The solid is then filtered off and analyzed by $^1$H NMR so as to confirm its chemical structure. The filtrate is evaporated and directly purified on a silica column. The fractions containing the desired product are combined and the solvent is evaporated off. The weight of product D obtained is 0.51 g, i.e. a synthesis yield of 69%.

The grafting of the chains was carried out in two steps:

-continued

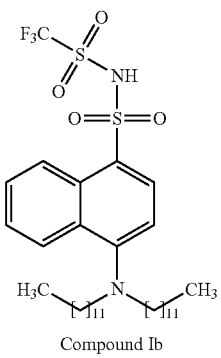

Compound Ib

Step n°1:

The product D (0.500 g, 1.4 mmol) is dissolved in 50 ml of DMF, in a 100 ml round-bottomed flask under an inert atmosphere. Triethylamine (0.59 ml, 3 eq) is added to the reaction medium with stirring. Finally, 1-bromododecane (0.84 ml, 2.5 eq) is added to the solution. The reaction medium is stirred at 70° C. for 48 h. 40 ml of deionized water and 2 ml of 2M HCl aqueous solution are added and the aqueous phase is extracted three times with 30 ml of dichloromethane. The product is purified on a silica column (MeOH/DCM) and the fractions containing the desired product are combined and evaporated. The monosubstituted product E is obtained in the form of a yellowish powder (0.460 g, 64% synthesis yield).

Step n°2:

The product E (0.460 g, 0.8 mmol) is dissolved in 50 ml of DMF, in a 100 ml round-bottomed flask under an inert atmosphere. Triethylamine (0.37 ml, 3 eq) is added to the reaction medium with stirring. Finally, 1-iodododecane (0.55 ml, 2.5 eq) is added to the solution. The reaction medium is stirred at 70° C. for 48 h. 40 ml of deionized water and 2 ml of 2M HCl aqueous solution are added and the aqueous phase is extracted three times with 30 ml of dichloromethane. The product is purified on a silica column (MeOH/DCM) and the fractions containing the desired product are combined and evaporated. The product F is obtained in the form of a brown powder (0.503 g, 82% synthesis yield).

Characterization of the Liquid Crystal $^1$H NMR (400 MHz; MeOD; 300 K): δ ppm 8.7 (d, 1H); 8.0 (d, 1H); 7.9 (d, 1H); 7.5 (dd, 1H); 7.4 (dd, 1H); 6.6 (d, 1H); 3.2 (d, 2H); 3.0 (d, 2H); 1.6 (m, 4H); 1.4 (m, 36H); 0.88 (t, 6H)

Its ATR 2-FTIR spectrum recorded on a Thermo Scientific Nicolet 6700 apparatus is represented in FIG. 4.

For the SAXS analysis, the sample is placed between two kapton films under an inert atmosphere and measured on a SAXS line. A rotating copper anode and a Vantec 2000 detector are used. The signal obtained is a ring of equivalent density (thus the material is isotropic); after radial integration, the 2D spectrum represented in FIG. 5 is obtained. The organized state of this material is characterized by the presence of Bragg peaks. The spectrum of the product Ib is characteristic of a structure in the form of lamellae (ratio 1:2).

EXAMPLE 3

Characterization of the Ionic Conductivities of the Compounds of Examples 2 and 3

The conductivity measurements are carried out in a CESH cell (Biologic) between two blocking electrodes. A potential difference of 50 mV is applied between the two blocking electrodes and a frequency scan between 5 MHz and 100 mHz is used. The EIS spectra obtained are modeled by equivalent electrical circuits (R1+R2/Q2+W) to determine the resistance of the electrolyte.

The results obtained are represented in FIG. 6 (ionic conductivity in $S \cdot cm^{-1}$ as a function of 1000/T, where T is the temperature in Kelvin). For the purposes of comparison, compounds not in accordance with the invention, termed 16-ANLi and 14-AN-Li, having the following formulae,

[Chem 9]

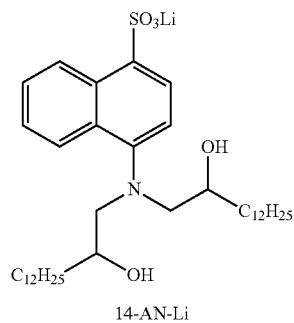

14-AN-Li

[Chem 10]

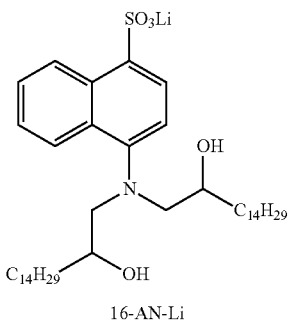

16-AN-Li were prepared according to the indications given in document EP 3 353 262 and tested under the same conditions as compounds Ia and Ib according to the invention.

It appears that only the thermotropic ionic liquid crystal molecules Ia and Ib in accordance with the invention have an ionic conductivity that can reach up to $10^{-5}$ $S \cdot cm^{-1}$ at 103° C., i.e. 100 times greater than that measured for the compounds not in accordance with the invention. In addition, compound Ib has a conductivity that is up to an order of magnitude greater than that of compound Ia. A conductivity of $10^{-4}$ $S \cdot cm^{-1}$ is in fact obtained from 75° C.

These results demonstrate the great efficiency of the thermotropic ionic liquid crystal molecules in accordance with the invention as an electrolyte in an electrochemical system, in particular in a lithium battery.

The invention claimed is:

1. A process for preparing an electrochemical system comprising:

preparing an electrolyte comprising thermotropic ionic liquid crystal molecules according to formula (I):

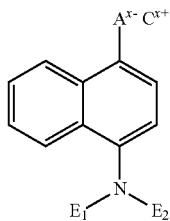

formula (I)

wherein:
E$_1$ and E$_2$, which may be identical or different, represent, independently of one another, a linear, saturated, and unsubstituted C$_{11}$ to C$_{13}$ alkyl radical,
A$^{x-}$ represents a sulfonate anion or a sulfonylimide anion —SO$_2$—N$^-$—SO$_2$CF$_3$,
C$^{x+}$ is an Li$^+$ cation, and
wherein thermotropic ionic liquid crystal molecules are in a mesomorphic state; and
employing said electrolyte in the electrochemical system.

2. The method according to claim 1, wherein E$_1$ and E$_2$ are identical.

3. The method according to claim 1, wherein -A$^{x-}$ is the sulfonate anion.

4. The method according to claim 1, wherein the thermotropic ionic liquid crystal molecules have a structure:

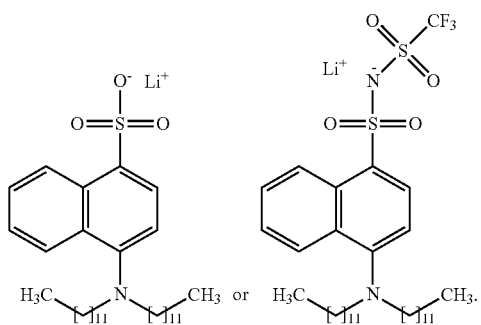

5. The method according to claim 1, wherein E$_1$ and E$_2$ are dodecyl radicals.

6. An electrolyte comprising thermotropic ionic liquid crystal molecules having formula (I):

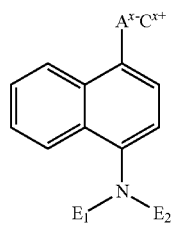

formula (I)

wherein:
E$_1$ and E$_2$, which may be identical or different, represent, independently of one another, a linear, saturated, and unsubstituted C$_{11}$ to C$_{13}$ alkyl radical,
A$^{x-}$ represents a sulfonate anion or a sulfonylimide anion —SO$_2$—N$^-$—SO$_2$CF$_3$,
C$^{x+}$ is an Li$^+$ cation, and
wherein thermotropic ionic liquid crystal molecules are in a mesomorphic state.

7. The electrolyte according to claim 6, wherein the electrolyte has a viscosity of greater than or equal to 10 mPa.s at a temperature of between −60° C. and 300° C.

8. The electrolyte according to claim 6, wherein the electrolyte has an ion conductivity at 20° C. of greater than or equal to $10^{-7}$ S.cm$^{-1}$.

9. The electrolyte according to claim 6, wherein the electrolyte has an ionic conductivity of greater than $10^{-4}$ S.cm$^{-1}$ at 100° C. and an ionic conductivity at 150° C. of greater than or equal to $10^{-3}$ S.cm$^{-1}$.

10. An electrochemical system comprising the electrolyte according to claim 6 and an electrode.

11. The electrochemical system according to claim 10, wherein the electrochemical system is a battery.

12. The electrochemical system according to claim 11, wherein the electrochemical system is a lithium battery.

13. The electrochemical system according to claim 10, wherein the electrolyte is impregnated in a porous separator.

14. A porous separator impregnated with the electrolyte according to claim 6.

* * * * *